United States Patent [19]
Williams

[11] Patent Number: 5,522,400
[45] Date of Patent: Jun. 4, 1996

[54] LOCKING CATHETER SYSTEM

[76] Inventor: Jeffrey T. Williams, 198 Parker Dr., Grayslake, Ill. 60030

[21] Appl. No.: 344,178

[22] Filed: Nov. 23, 1994

[51] Int. Cl.⁶ .................................................. A61M 25/61
[52] U.S. Cl. ............................................................ 128/772
[58] Field of Search ..................... 604/280, 283, 604/165, 281, 146; 128/772

[56] References Cited

U.S. PATENT DOCUMENTS

| | | | |
|---|---|---|---|
| 3,638,653 | 2/1972 | Berry | 606/146 |
| 4,011,873 | 3/1977 | Hoffmeister | 606/146 |
| 4,033,331 | 7/1977 | Guss et al. | 604/281 |
| 4,613,329 | 9/1986 | Bodicky | 604/165 |
| 4,740,195 | 4/1988 | Lanciano | 604/95 |
| 4,886,067 | 12/1989 | Palermo | 128/772 |
| 4,940,062 | 7/1990 | Hampton et al. | 128/772 |
| 5,117,839 | 6/1992 | Dance | 604/168 |
| 5,129,887 | 7/1992 | Euteneur et al. | 604/165 |
| 5,228,452 | 7/1993 | Samson | 128/772 |
| 5,304,140 | 4/1994 | Kugo et al. | 604/281 |
| 5,327,905 | 7/1994 | Avitall | 128/772 |

*Primary Examiner*—Paul J. Hirsch
*Attorney, Agent, or Firm*—Laff, Whitesel, Conte & Saret

[57] ABSTRACT

A locking catheter system including a flexible catheter having a restraining portion such as a pigtail, malecot rib or J-curve at its distal end and a flexible filament extending therefrom to attaching means at the other end of the catheter. The attaching means comprise a compressible suture-sealing bushing through which the flexible filament is passed and locked in place.

20 Claims, 6 Drawing Sheets

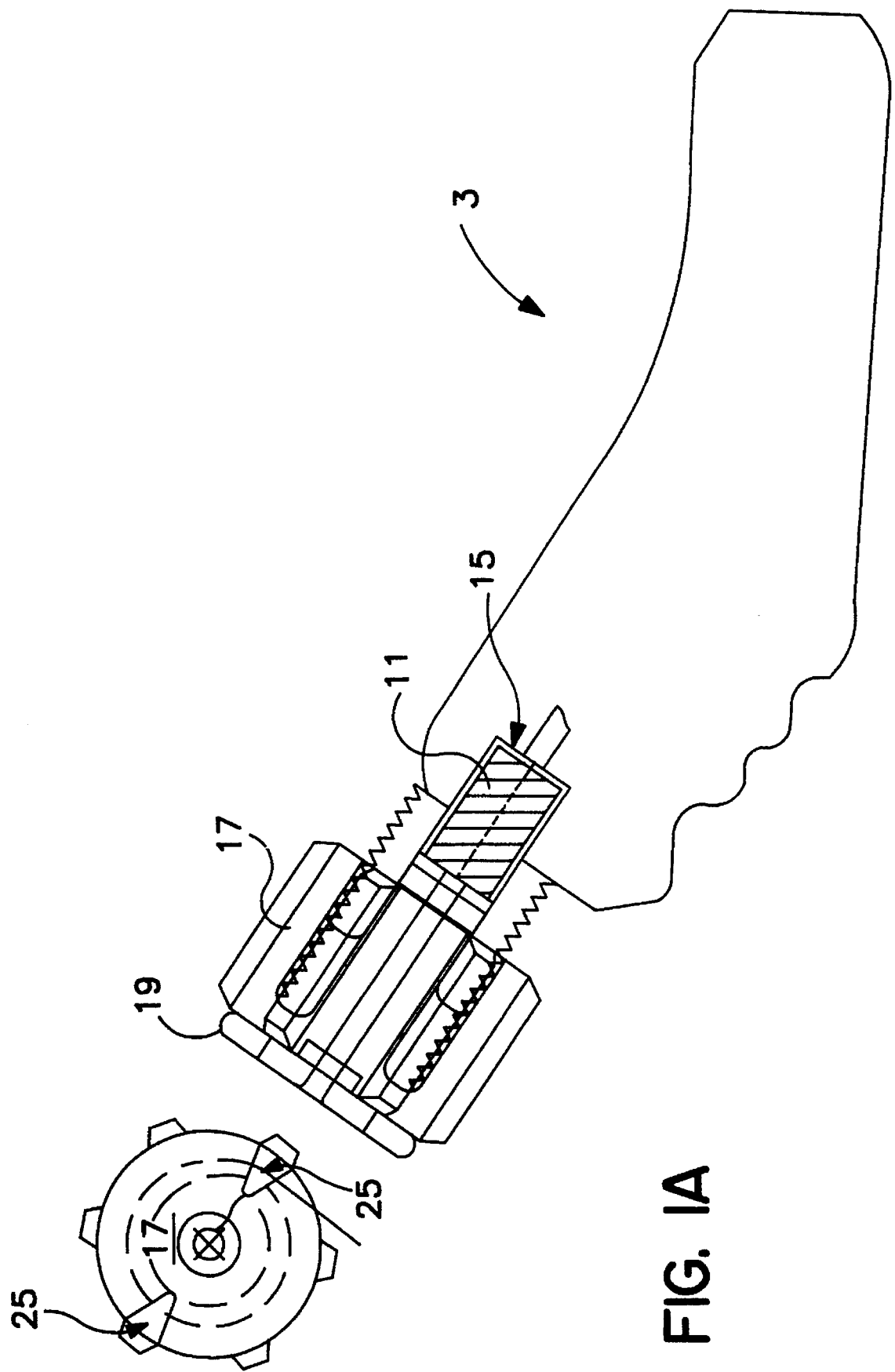
FIG. IA

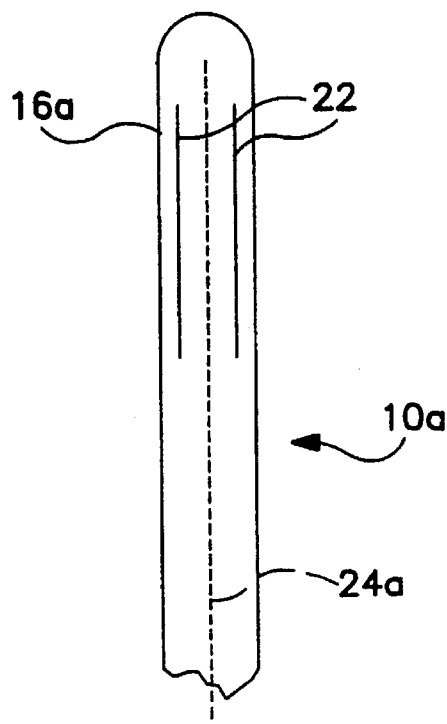
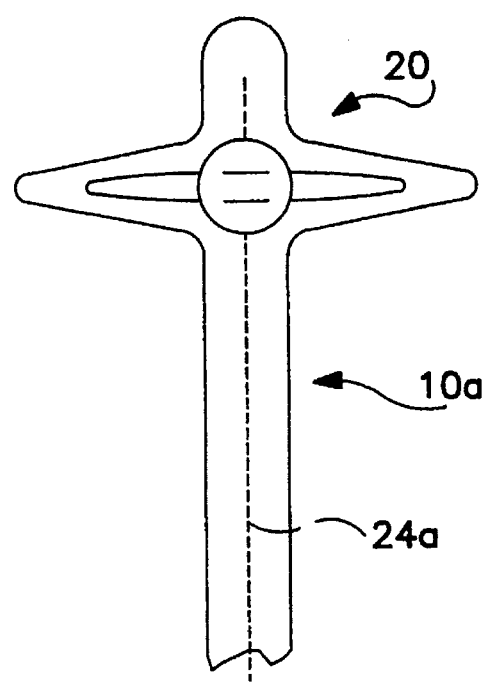
FIG. 2A  FIG. 2B
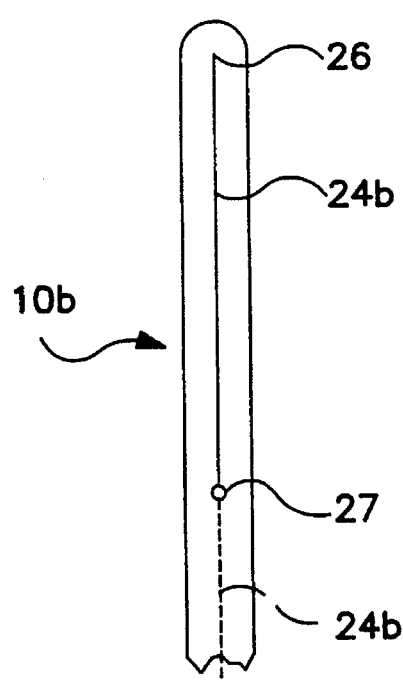
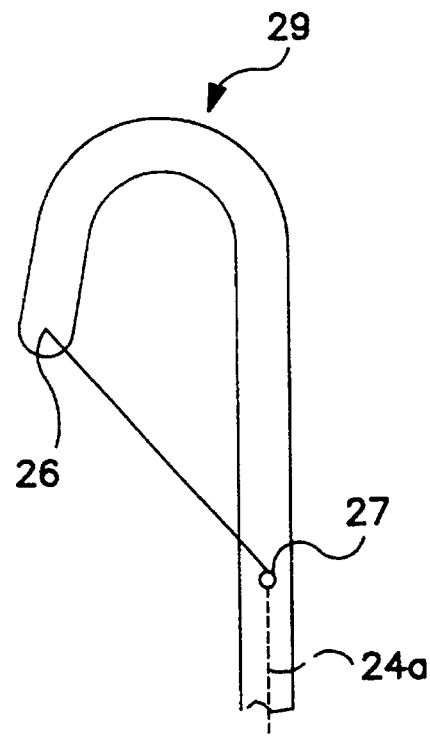
FIG. 3A  FIG. 3B

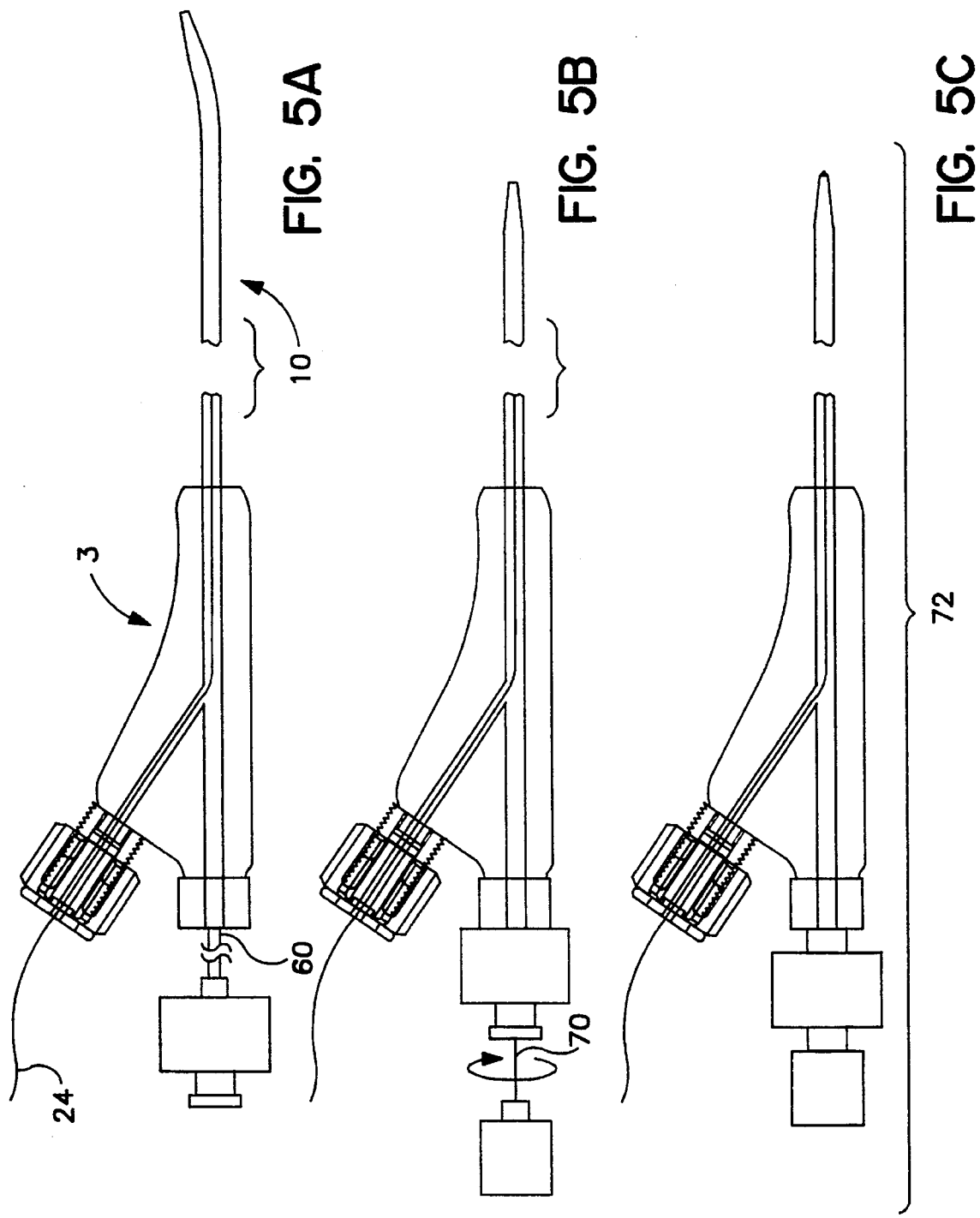

LOCKING CATHETER SYSTEM

BACKGROUND OF THE INVENTION

This invention relates generally to medical (including veterinary) catheters and, more particularly, to a unique medical catheter designed to be removably anchored within a body cavity by forming and maintaining an obstruction to removal in the form of a restraining portion in the distal end of the catheter until it is desired to withdraw the catheter from the cavity.

Flexible catheters are widely used for percutaneous drainage of fluid collections and percutaneous nephrostomy. They are also used for drainage of abscesses, bile, cysts, pleural effusions, empyemas, and other mediastinal collections. In such applications, the catheters are typically inserted either over a previously emplaced guide wire or by direct puncture using a trocar styler.

Once in position in a body cavity, it is desirable to anchor the catheter before drainage begins. This may be done by forming a restraining portion in the distal end of the catheter in the form of a pigtail, a J-curve or a malecot rib. In order to reliably anchor and then later easily remove the catheter, it is important to be able to lock and unlock the restraining portion in the distal end of the catheter from the proximal end of the catheter, where it protrudes from the body.

One technique for locking a pigtail in the distal end of a drainage catheter is described in U.S. Pat. No. 4,740,195 to Lanciano. That patent describes a suture attached to the distal end of the catheter which is held in position in a stopcock-type of locking mechanism in its proximal end. Another prior art device for locking a pigtail in the distal end of a drainage catheter with a suture arrangement uses a latex sleeve to cover the suture as it exits from a hole the wall of the catheter at its proximal end to thereby holds it in place and also reduce leakage. Both of these prior art techniques are unsatisfactory since they permit liquid leakage along the suture as it emerges from the catheter and gas leakage at the hole in the wall of the catheter.

SUMMARY OF THE INVENTION

The present invention comprises a locking catheter system with a flexible catheter having a locking mechanism at its proximal end and a restraining portion at its distal end. The restraining portion may be a pigtail, a J-curve or a malecot rib. Means, in the form of a flexible filament such as a suture extends from the restraining portion of the catheter to the proximal end of the catheter for drawing the distal end of the catheter toward the proximal end to form or manipulate the restraining portion. Ideally, the flexible filament is non-woven and non-porous.

The heart of the invention lies in improved means, located at the proximal end of the catheter, for removably attaching the proximal end of the flexible filament to the catheter in a way which is secure, convenient and largely free of leakage. The improved attaching means include a suture retention leg which is integral with the catheter and includes a compressible bushing through which the flexible filament is passed. The bushing sits in a cavity at the proximal end of the suture retention leg of the catheter and is compressed by screwing down upon a locking cap having a plunger which bears against the bushing. Due to the sealing properties of the compressible bushing, liquid and gaseous leakage from the catheter is minimized or eliminated, both when the bushing is in an uncompressed condition and when it is in a compressed condition.

BRIEF DESCRIPTION OF THE DRAWING

The features of this invention which are believed to be novel are set forth with particularity in the appended claims. The invention, together with its objects and advantages, may be best understood by reference to the following description, taken in conjunction with the following drawings, in which like reference numerals identify like elements in the several figures, and in which:

FIG. 1A is an enlarged elevation view of the suture retention leg only;

FIGS. 2A and 2B are diagrammatic representations of a restraining portion in the form of a malecot rib;

FIGS. 3A and 3B are diagrammatic representations of the invention showing the restraining means in the form of a J-curve;

FIGS. 5A, 5B and 5C are partial elevation views of the catheter of the invention, illustrating the use of a stiffening cannula and a trocar stylet in conjunction with the compression housing.

DESCRIPTION OF THE PREFERRED EMBODIMENT

Figure 1:
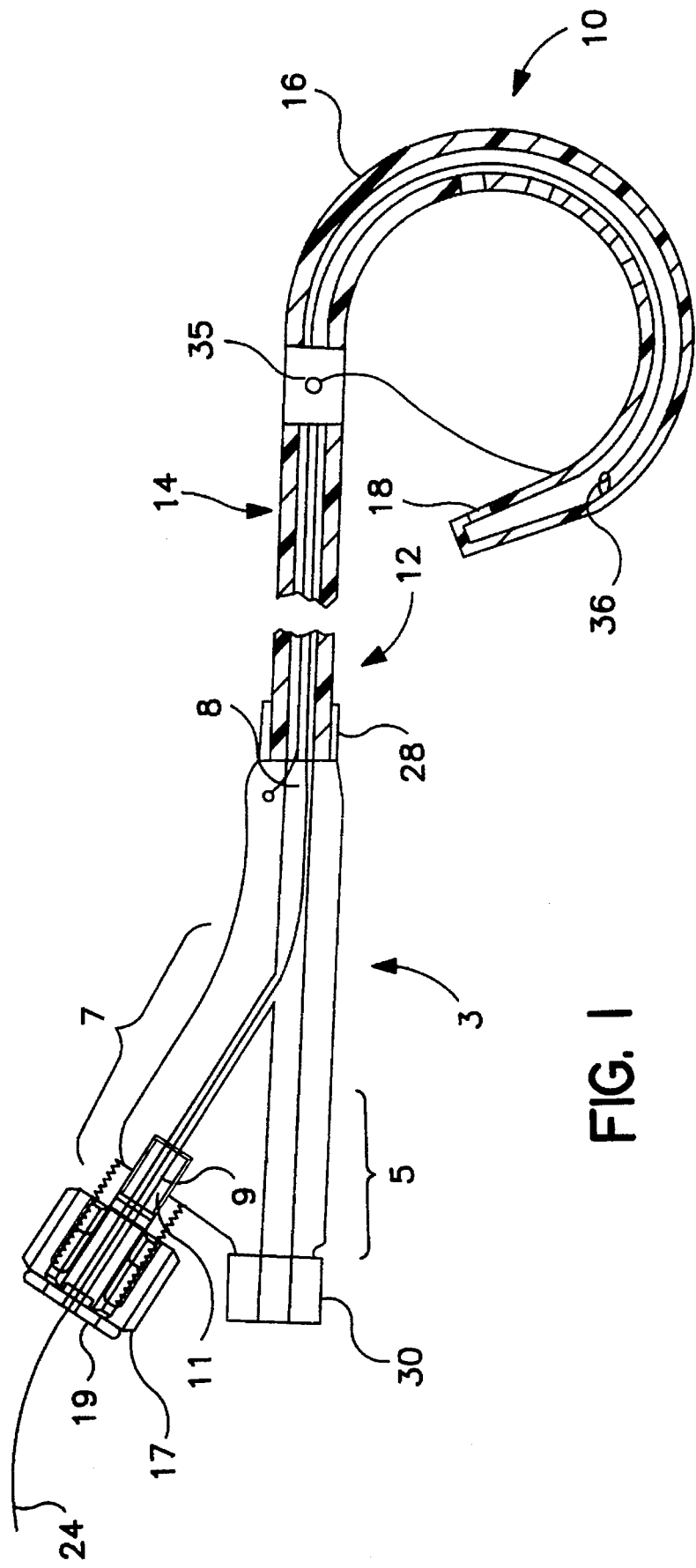
FIG. 1 is a elevation view of the catheter of the invention, cut-away to show the flexible filament positioned within the suture retention leg of the catheter, with the filament emerging from a compressible bushing.

Turning now to FIG. 1, there is depicted a hollow thermoplastic catheter 10 having a proximal end 12, a distal end 14 and a restraining portion 16. The restraining portion of the catheter includes at least one drainage hole 18. Catheter 10 may be made of polyurethane, polyethylene, EVA, nylon, or any other suitable flexible biomaterial. The respective length of the elongated portion and the restraining portion may vary, according to the desired application.

Restraining portion 16 is depicted in FIG. 1 as a pigtail which was preformed in of the distal end of the catheter. Other restraining means may be used, such as the malecot rib fixation 20 depicted in FIG. 2B. As seen in FIG. 2A, longitudinal slits 22 are located in the restraining portion 16a of the catheter 10a, so that, as suture 24a is drawn proximally, a malecot rib 20 is formed (FIG. 2B).

Another restraining means is depicted in FIGS. 3A and 3B. In this embodiment, catheter 10b is straight and suture 24b is attached to the distal end of the catheter at 26 and passes into the hollow interior of the catheter through hole 27. Thus, when suture 24b is drawn proximally, a J-curve 29 is formed in the distal end of the catheter, as depicted in FIG. 3B.

Returning to FIG. 1, the proximal end of the catheter includes a locking system housing having a drainage leg 5 and a suture retention leg 7. The proximal end of the catheter includes an optional stress relief sleeve 28 to facilitate handling of the catheter. The locking system housing 3 has leur lock 30 and is attached to the stress relief sleeve (or directly to the catheter, if no stress relief sleeve is present) to facilitate attachment of the catheter to appropriate drainage devices (not shown) via the drainage leg of the housing 5.

One end of suture 24 is attached internally to the proximal end of the catheter by molding, gluing, welding, mechanically retaining or otherwise attaching that end of the suture into the interstitial space between locking system housing 3 and stress relief sleeve 28 (or directly to the catheter, if no stress relief sleeve is present). Suture 24 is then passed through the hollow interior of the catheter to distal end 14 thereof, where it emerges through a hole 36.

The suture re-enters the catheter through a hole 35 in the restraining portion of the catheter and returns by way of the interior of the catheter to the proximal end of the catheter, where it enters a bore 8 in suture retention leg 7 and emerges from a longitudinal bore 9 in a compressible bushing 11. The bore is sized to seal against the outer surface of the suture while permitting it to slide when pulled, so long as the bushing is in an uncompressed state.

Figure 1B:
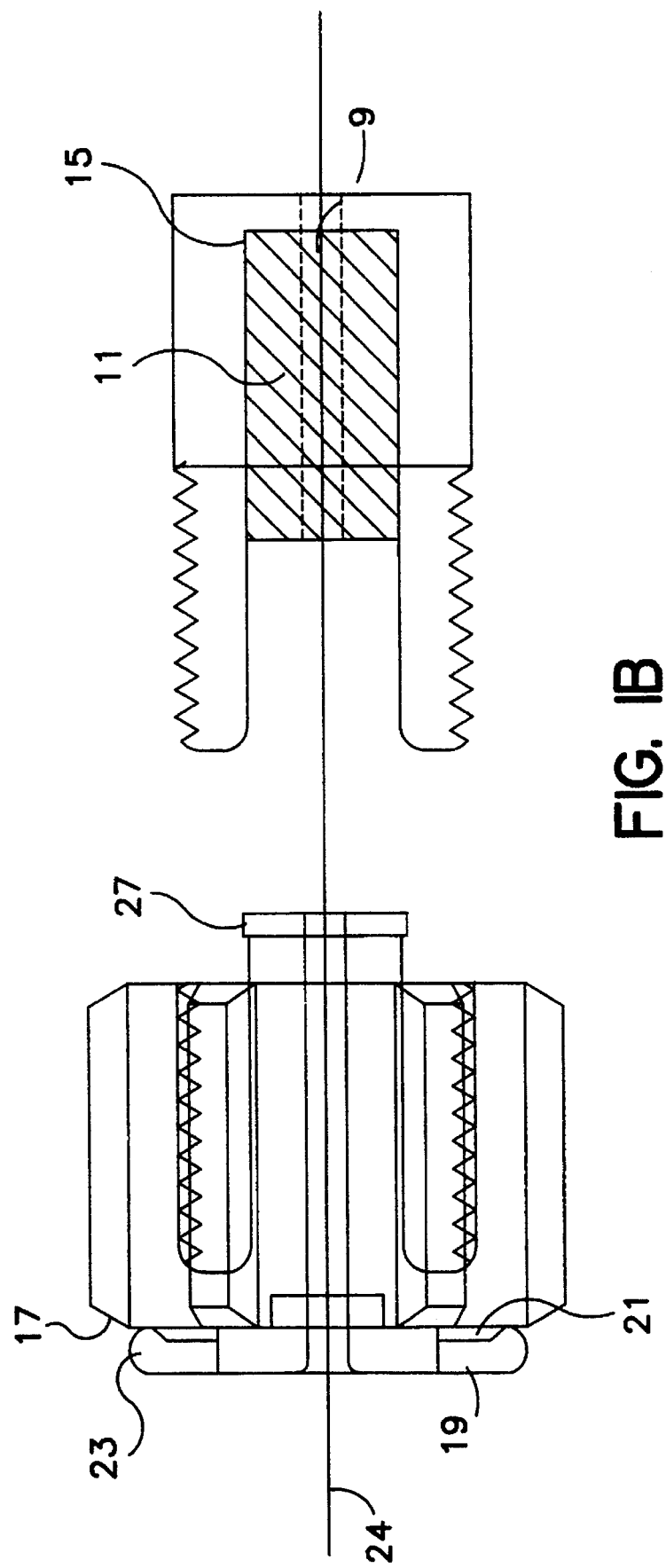
FIG. 1B is an exploded view of the suture retention leg showing all the components of the retention means of the invention.

As illustrated in FIGS. 1A and 1B, compressible bushing 11 fits snugly in a bushing cavity 15 at the proximal end of the retention leg. The bushing may be made of any material which will firmly hold the suture when it is in a compressed state, but will permit the suture to be pulled through the bushing when it is in an uncompressed state. It is important to note that a liquid and gas seal is maintained irrespective of the state of the compressible bushing. Bushing compression only alters the retention force on the suture. The bushing is placed in a compressed state by screwing down on locking cap 17 with plunger 27 engaging the compressible bushing. When the locking cap is unscrewed, the bushing will return to its uncompressed state.

The bushing may be made of latex, silicone, thermoplastic elastomer or other compressible material with the necessary sealing properties, with latex being preferred. Due to the sealing properties of the bushing, a tight seal to the outer surface of the suture is obtained and leakage of liquids and gases from the catheter is minimized or eliminated.

The locking cap also incorporates a protected area 21 for storing the free end of the suture after the restraining means of the catheter is fixed in place (e.g., as in FIGS. 1, 2B, 3B, 4A and 5A). This protected area is located under locking ring 19 which is made of a resilient material and includes an annular lip 23 on its underside. Thus, the free end of the suture is wound into one of the slots 25 at the outer edge of the locking ring and forced under the lip which flexes out of the way to store the excess suture in "spool" form in the protected area.

The flexible catheter of the invention may be inserted over a guidewire or by direct puncture using a trocar stylet. Guidewire insertion proceeds as illustrated in part by FIGS. 4A and 4B.

Figure 4A:
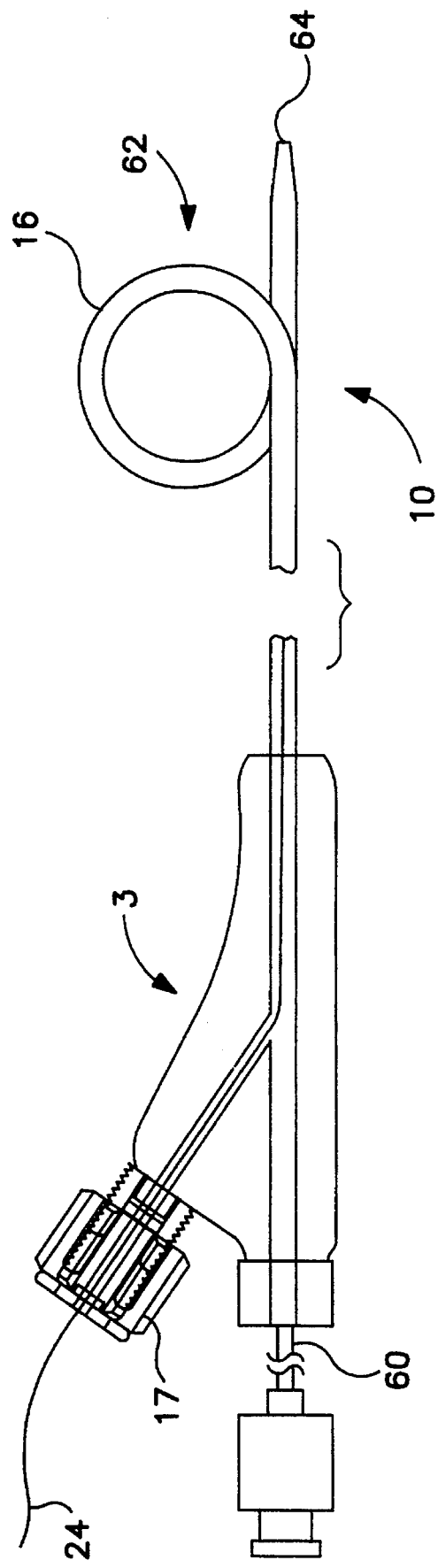
FIGS. 4A and 4B are elevation views of the catheter with pigtail restraining means of the invention illustrating insertion of the catheter over a stiffening cannula into the catheter.
Figure 4B:
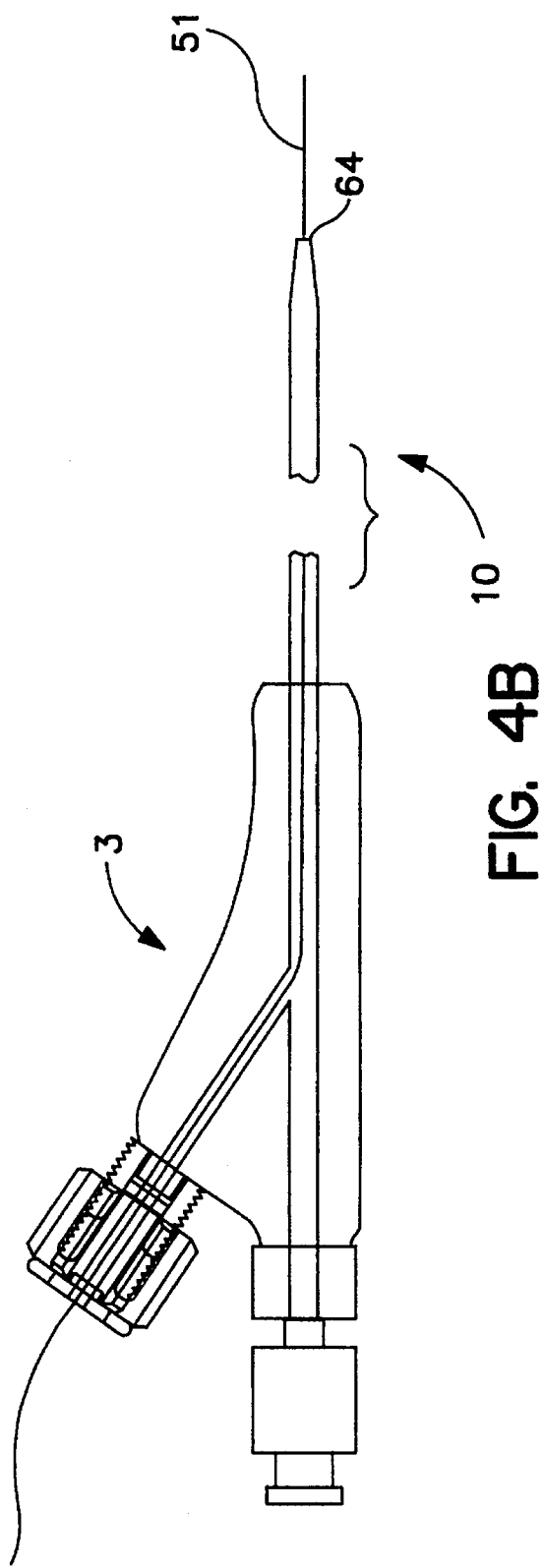

First, a drainage site is selected and prepared using standard techniques, a guidewire 51 is inserted into the drainage site through a needle and the tract is dilated. Next a stiffening cannula 60 is inserted into catheter 10 while it is straightened ahead of the advancing cannula. Once the stiffening cannula is in place, as shown in FIG. 4B, the cannula is locked into locking system housing 3. The resulting catheter/cannula assembly is advanced over the guidewire into the site.

Next, the stiffening cannula is unlocked and the catheter advanced while the cannula is held stationary. The stiffening cannula and guidewire are then removed so that the restraining means (pigtail 62) returns to its original shape (FIG. 4A).

The distal tip of the catheter 64 is then moved into place in accordance with the invention by pulling back on suture 24 while monitoring under fluoroscopy until the pigtail is secured, then screwing down on locking cap 17 to lock the suture in place and winding the free end of the suture under the suture locking ring. The drainage leg of the locking system housing is then attached to an appropriate drainage device and fluid is drained by suction or gravity.

When a direct puncture technique is used, as illustrated in FIGS. 5A–C, the drainage site is selected and prepared using standard techniques, the stiffening cannula 60 is inserted while straightening the catheter ahead of the cannula, (as described above), and the stiffening cannula is locked into catheter locking system housing 32. Then, a trocar stylet 70 is advanced into place and locked into the hub of the stiffening cannula (FIG. 5B). The resulting catheter/cannula/ trocar stylet assembly 72 is then advanced into the site and the trocar stylet removed. If desired, a guidewire may then be inserted to aid in placement.

Next, the stiffening cannula is unlocked and the catheter advanced while the cannula is held stationary whereupon the stiffening cannula and guide wire are removed. Then, the distal tip of pigtail 62 is positioned by pulling back on the free end of the suture and locking it in place by screwing down on locking cap 17 to lock the suture in place and winding the free end of the suture under the suture locking ring, as described above. The catheter is then attached to appropriate drainage device and fluid is drained by suction or gravity from the drainage leg of the catheter.

Once the drainage procedure is completed and the catheter is to be removed, the drainage device is disconnected from the catheter, the suture is unwound from the locking ring, and the locking cap is unscrewed to release the suture.

The catheter may now be gently pulled from the cavity. If access is to be maintained, an appropriate guide wire (not shown) may be used to assist in removal and subsequent placement of another catheter.

While the present invention is described above in connection with specific embodiments, the invention is intended to cover all alternatives, modifications or equivalents that may be included within its sphere and scope, as defined by the appended claims.

What we claim is:

1. A locking catheter system comprising:
   a flexible catheter having a restraining portion at its distal end;
   a flexible filament, extending from the restraining portion to the proximal end of the catheter, for drawing the restraining portion toward the proximal end; and
   means, at the proximal end of the catheter, for removably fixing the flexible filament in place after the restraining portion is drawn toward the proximal end,
   the fixing means comprising a compressible bushing having a longitudinal bore for sealingly and slidingly holding the flexible filament; and means for compressing the bushing to lock the flexible filament in place.

2. The locking catheter of claim 1 in which the restraining portion is a preformed curve in the distal end of the catheter.

3. The locking catheter of claim 2 in which the preformed curve is in a pigtail shape.

4. The locking catheter of claim 2 in which the preformed curve is a malecot rib.

5. The locking catheter system of claim 1 in which the flexible filament is non-woven and non-porous.

6. The locking catheter system of claim 1 in which the compressible bushing is made of latex.

7. The locking catheter system of claim 1 in which the compressible bushing is made of silicone.

8. The locking catheter system of claim 1 in which the compressible bushing is made of thermoplastic elastomer.

9. The locking catheter system of claim 1 in which the compressible bushing is made of compressible sealing material.

10. The locking catheter of claim 1 in which means are provided for storing the flexible filament.

11. The locking catheter of claim 10 in which the storing means comprises an externally accessible annular protected space into which the flexible filament may be wound.

12. The locking catheter system of claim 1 in which the flexible filament is attached to the proximal end of the catheter by molding, gluing, welding, mechanically retaining or other suitable means.

13. A locking catheter system comprising:

a flexible catheter having a restraining portion in the form of a preformed curve portion at its distal end;

a flexible filament, extending from the restraining portion to the proximal end of the catheter, for drawing the restraining portion toward the proximal end; and means, at the proximal end of the catheter, for removably fixing the flexible filament in place after the restraining portion is drawn toward the proximal end, the fixing means comprising a compressible bushing having a longitudinal bore for sealingly and slidingly holding the flexible filament; and means for compressing the bushing to lock the flexible filament in place.

14. The locking catheter of claim 13 in which the curved portion is in the shape of a malecot rib.

15. The locking catheter of claim 13 in which the curved portion is in the shape of a J-curve.

16. The locking catheter system of claim 13 in which the flexible filament is non-woven and non-porous.

17. The locking catheter system of claim 13 in which the compressible bushing is made of latex.

18. The locking catheter system of claim 13 in which the compressible bushing is made of silicone.

19. The locking catheter system of claim 13 in which the compressible bushing is made of thermoplastic elastomer.

20. The locking catheter system of claim 13 in which the compressible bushing is made of compressible sealing material.

* * * * *